United States Patent [19]
Flickinger

[11] Patent Number: 5,906,198
[45] Date of Patent: May 25, 1999

[54] NASAL NEBULIZER

[76] Inventor: William J. Flickinger, 315 Linda Ct., Lino Lakes, Minn. 55014

[21] Appl. No.: 08/891,940

[22] Filed: Jul. 14, 1997

Related U.S. Application Data

[60] Provisional application No. 60/021,813, Jul. 16, 1996.

[51] Int. Cl.$^6$ .................................................. A61M 11/00
[52] U.S. Cl. ................................. 128/200.21; 128/203.22
[58] Field of Search ........................... 128/200.11–200.29, 128/203.22, 203.13, 203.29, 207.18, 204.12, 203.18

[56] References Cited

U.S. PATENT DOCUMENTS

| | | | |
|---|---|---|---|
| Re. 33,717 | 10/1991 | Suoboda ............................ | 128/200.21 |
| 59,562 | 11/1866 | Cutter . | |
| 258,632 | 5/1882 | Cooper . | |
| 746,749 | 12/1903 | Seidel ................................ | 128/203.18 |
| 2,266,704 | 12/1941 | Fox et al. ........................... | 128/200.21 |
| 2,385,808 | 10/1945 | Goldbert ........................... | 128/200.21 |
| 2,566,806 | 9/1951 | Miller ................................ | 128/203.22 |
| 2,826,194 | 3/1958 | Golden .............................. | 128/200.14 |
| 3,066,669 | 12/1962 | De Melfy .......................... | 128/203.22 |
| 3,269,389 | 8/1966 | Meurer et al. .................... | 128/200.14 |
| 4,012,473 | 3/1977 | Lindsey . | |
| 4,484,577 | 11/1984 | Sackner . | |
| 4,699,136 | 10/1987 | Xrauser ............................. | 128/203.22 |
| 5,086,765 | 2/1992 | Levine . | |
| 5,209,225 | 5/1993 | Glenn . | |
| 5,287,847 | 2/1994 | Piper . | |
| 5,299,565 | 4/1994 | Brown . | |
| 5,586,551 | 12/1996 | Hilliard ............................. | 128/203.29 |
| 5,649,530 | 7/1997 | Ballini .............................. | 128/200.14 |

*Primary Examiner*—John G. Weiss
*Attorney, Agent, or Firm*—Carstens Yee & Cahoon, LLP; Colin P. Cahoon

[57] ABSTRACT

A nebulizer device for use in administering liquid medication and fluids to the nasal passages utilizing the venturi and siphon effects to produce a mist in two air streams from one external air source. The nebulizer device comprises two major sections, a cap section and a reservoir section, with the cap section having an integrally molded pair of siphon tubes which fit over opposing pairs of air tubes attached to the reservoir section. Pressurized air introduced into the reservoir section travels through the air tubes and exits small diameter orifices which are position relative to similar small diameter orifices of the siphon tubes. This interface creates a venturi effect whereby liquid medication is siphoned from the bottom of the reservoir section, through the space provided between the inside diameter of the siphon tubes and the outside diameter of the air tubes, and exits as mist or liquid droplets through the small orifices of the siphon tubes. These two mist streams are directed to the two nostrils of the patient, while a nose shield attached to the cap section keeps the liquid medication out of the patient's eyes.

17 Claims, 2 Drawing Sheets

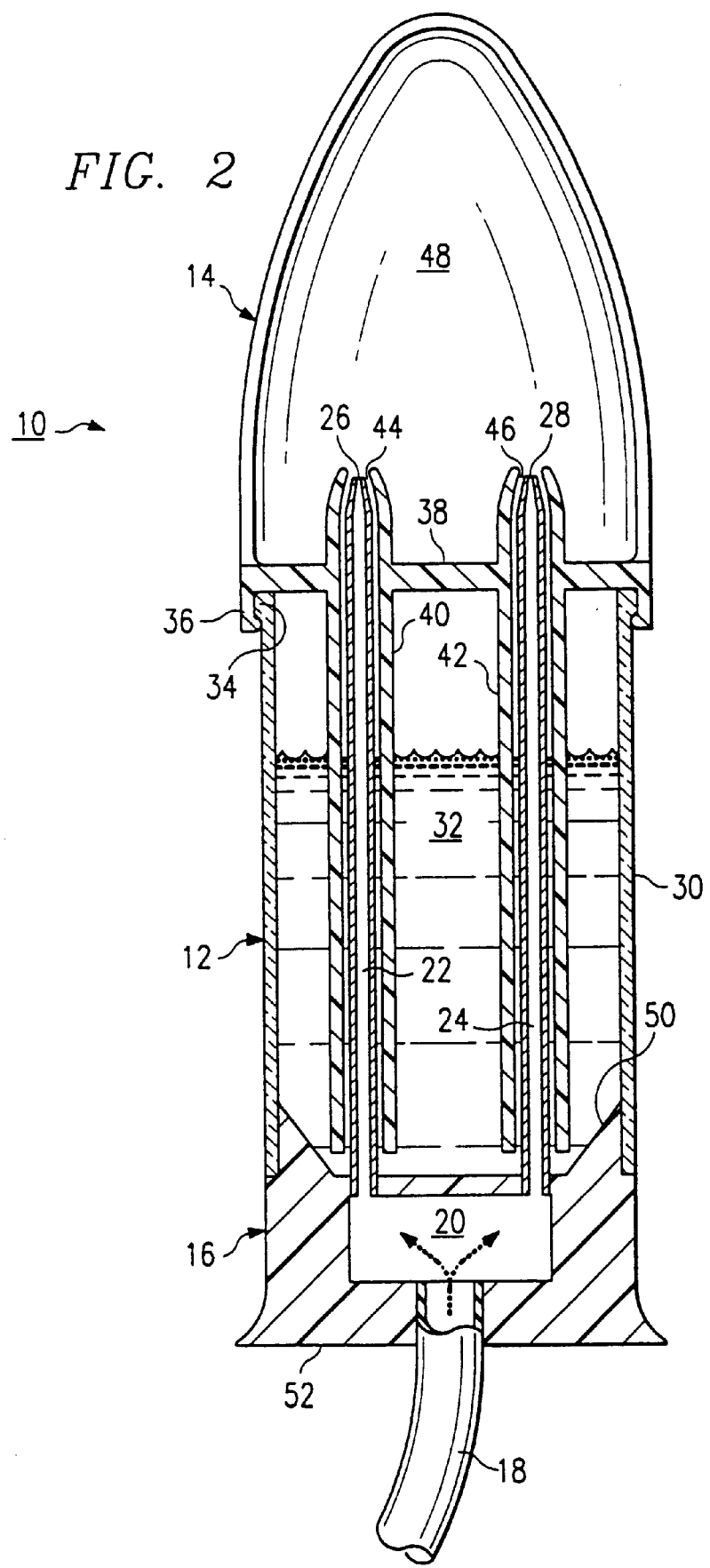

NASAL NEBULIZER

CROSS-REFERENCE TO RELATED APPLICATIONS

This application is the non-provisional submission of a provision application of the same title filed on Jul. 16, 1996 and assigned application Ser. No. 60/021,813.

BACKGROUND OF THE INVENTION

The present invention relates to devices used for administering liquid medication in mist or liquid droplet form to a patient. The particular design of the present invention is directed to administering the liquid medication to the nasal passages of a patient while emphasizing simplicity in design, ease of manufacture, and simplicity of use.

Devices used for administering liquid medication to a patient by way of mist or liquid droplets are generally called nebulizers. Present art nebulizers are designed with a single exist port whereby mist or liquid droplets exit the device to be inhaled by the patient. The mist from these present art nebulizers leaves the device in a low pressure flow rate as a result of baffles or air dams that redirect a venturi jet stream of liquid droplets as the liquid medication is drawn from a liquid reservoir in the device. These devices are best suited for the inhalation of the liquid droplets through the patient's mouth. Certain medical conditions, however, require the introduction of liquid droplets through the patient's nasal passages. The present art nebulizers, with a single orifice and typically low pressure flow rates, are not effective in introducing liquid medication through the two nostrils of a patient, particularly when the patient's nasal passages are congested or otherwise obstructed.

Accordingly, one principle object and purpose of the present invention is to provide a nebulizer which expels a liquid medication mist in two separate mist streams which can be directed to the nostrils of a patient. It is an additional objective and purpose of the present invention to provide a nasal nebulizer which is simply in construction, easy to produce, and simple to use.

SUMMARY OF INVENTION

This invention relates to a nebulizer device designed to deliver liquid medication and fluids to the nasal passages of a patient utilizing the venturi and siphon effects to produce a mist in two air streams from one external air source. Unlike present art nebulizer devices, the present invention simultaneously administers medication in both nasal passages using a direct stream of medicine from an external air source. The invention utilizes a liquid reservoir incorporated with the nebulizer device and a cap sealing the reservoir having molded siphons. Pressurized air is introduced at the base of the liquid reservoir, is split into two separate air streams, and flows through two air tubes located internal to the liquid reservoir. These two air tubes extend above the reservoir fluid level and end in small diameter orifices.

After filling the reservoir with the fluid medication, the cap sealing the reservoir is placed on top of the reservoir such that two molded siphons, of slightly larger diameter than the two air tubes, are fitted over the two air tubes and encase all but the bottom of these air tubes within the fluid reservoir. The two siphon tubes protrude through the cap and end on the exposed side of the cap in small diameter orifices. The orifice restrictions of the siphon tubes and air tubes are oriented such as to create a venturi and siphon effect. Fluid in the reservoir is siphoned from the bottom of the siphon tubes through the reservoir cap and atomized by pressurized air flowing through the two air tubes. The resulting mist is intended to be blown into the nasal passages of the patient. The nebulizer invention also utilizes an eye shield to protect the patient's eyes from inappropriate application of medication.

This invention is distinguished from the present art in that it utilizes dual air nozzles for spraying mist into the nasal passages. In addition, present art nebulizers do not utilize the dual siphon system of siphon tubes molded into the reservoir cap. Present art nebulizers also do not utilize an eye shield to protect the patient's eyes from inappropriate application of liquid.

This present invention is a substantial improvement over the present art in providing a nebulizer device that is simple in design, easy to manufacture, and safely and effectively allows for the administration of fluid medication as a mist into a patient's nasal passages.

BRIEF DESCRIPTION OF THE DRAWINGS

Further objects and advantages of the present invention will become apparent from the following detailed description when read in conjunction with the accompanying drawings, in which:

FIG. 2 is a sectional view of the invention.

DETAILED DESCRIPTION OF PREFERRED EMBODIMENT

Figure 1:
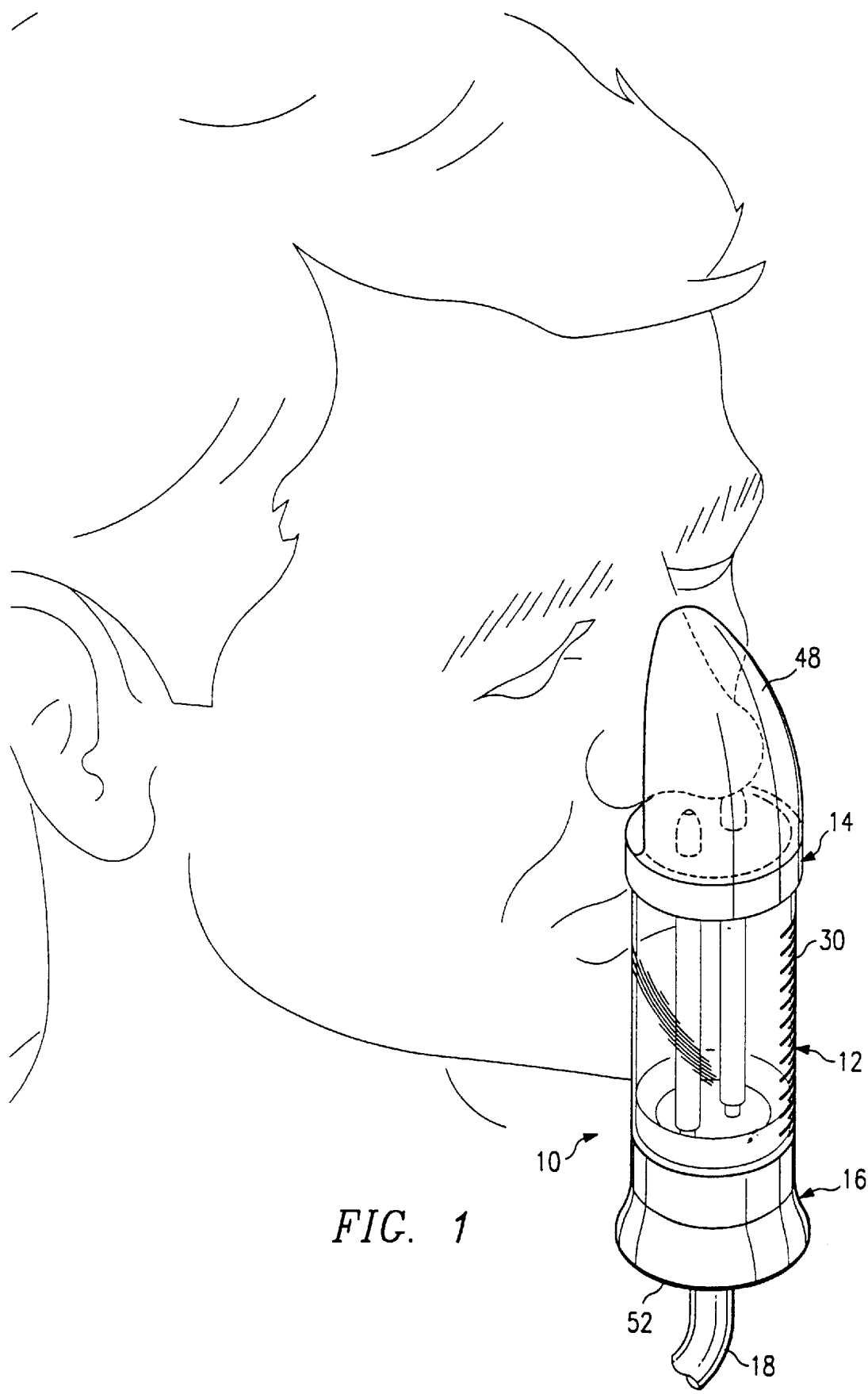
FIG. 1 is a perspective view of the invention being used by a patient.

FIG. 1 shows a preferred embodiment of the nebulizer invention 10 in use by a patient and illustrates the invention's major components. This nebulizer is constructed into two separate contiguous sections consisting of a reservoir section 12 and a cap section 14. Both FIGS. 1 and 2 show the reservoir section 12 and the cap section 14 joined, which is their relative position when the nebulizer 10 is in use or is being stored. In order to introduce a liquid medication into the device, however, it is necessary to pull the cap section 14 vertically away from the reservoir section 12, thereby exposing an opening at the top of the reservoir section 12 for the introduction of the medication.

Also shown in FIG. 1 is the base 16 of the reservoir section 12 and the nose shield 48 of the cap section 14. The nebulizer 10 can be constructed of any medically inert material, including glass, surgical steel, or plastic. In one preferred embodiment, the nebulizer 10 is constructed of molded plastic. The preferred embodiment shown in FIG. 1 utilizes a clear plastic construction of the cylinder 30 attached to the base 16, both of which are a part of the reservoir section 12. With a clear plastic construction, the cylinder 30 can be manufactured with graduated volume marks, thereby allowing an easy determination of the volume of fluid or medication contained within the reservoir section 12.

FIG. 2 is a sectional view of the nebulizer 10. Shown again are the two separate sections of the nebulizer 10, the reservoir section 12 and the cap section 14. Integrity is maintained between the reservoir section 12 and the cap section 14 by virtue of a friction or snap fit between a circumferential collar 36 of the cap section 14 and a circumferential lip 34 of the reservoir 12 section.

In the embodiment shown in FIG. 2, the reservoir section 12 consists of a clear cylinder 30 mounted on a base 16. The base 16 is constructed with a flat horizontal surface 52 to allow for easy storage and filling of the device and a circumferential angle 50 along the interface of the base with the fluid medication 32. This circumferential angle 50 creates a pooling effect in the reservoir section 12 which promotes efficient use of all of the fluid medication introduced into the nebulizer.

As is shown in both FIG. 1 and FIG. 2, pressurized gas, typically air, is introduced into the nebulizer 10 through a pressurized air inlet 18 located in the center of the flat horizontal surface 52 of the base 16. The pressurized gas flows into a pressurized gas chamber 20 and is then split into two streams through a first gas transporting tube 22 and a second gas transporting tube 24. The pressurized gas continues through the gas tubes 22, 24 and exits the reservoir section 12 at small diameter orifices 26, 28.

The gas tubes 22, 24 can be integrally molded with the base 16 or attached thereto with glue or some other sealing means. When the cap section 14 is not installed on the reservoir section 12, the gas tubes 22, 24 extend vertically from and perpendicular to the base 16, through the fluid medication 32, and protrude above the circumferential lip 34 of the reservoir section 12.

Turning now to the second section of the nebulizer 10, FIG. 2 also illustrates the individual components of the cap section 14. The cap section 14 comprises a disc-shaped cap base 38, integrally molded siphons or liquid transporting tubes 40, 42, a circumferential collar 36, and a nose shield 48. A first siphon 40 and a second siphon 42 are integrally molded components of the cap base 38. These siphons or liquid transporting tubes 40, 42 are tube shaped with interior diameters slightly larger than the exterior diameters of the gas tubes 22, 24 of the reservoir section 12. The siphons 40, 42 extend vertically from the bottom of the cap base 38 such that, when the cap section 14 is installed on the base section 16, the bottom of the siphons 40, 42 extend to nearly the lowest expected fluid level of the reservoir section 12. This allows fluid medication to enter the base of the siphons 40, 42 and proceed between the outer diameter of the gas tubes 22, 24 and the inner diameter of the siphons 40, 42 until being expelled by the pressurized air exiting small diameter orifices 26, 28 at the end of the gas tubes 22, 24.

The siphons 40, 42 also extend vertically above and perpendicular to the cap base 38. The upper end of the siphons 40, 42 are tapered to form small-diameter orifices 44, 46. The distance between the center of these orifices 44, 46 would be the approximate distance between the centers of the two nostril openings of a human patient. When the cap section 14 is installed on the reservoir section 12, the siphons 40, 42 enclose the gas tubes 22, 24, and the siphon orifices 44, 46 are positioned relative to the gas tube orifices 26, 28 as to create a venturi effect with the pressurized gas expelled from the gas tubes 22, 24. Fluid is thereby drawn through the siphons 40, 42 and is expelled through the siphon orifices 44, 46. The rate of delivery of the fluid medication as well as the mist characteristics can be adjusted by changing the gas pressure introduced at the pressurized air inlet 18, by changing the manufacturing specifications on the diameters of the orifices 26, 28, 44, 46, or by changing the manufacturing specifications for the relative positions of the orifices 26, 28, 44, 46.

Attached to the cap base 38 is a molded nose shield 48. As illustrated in FIG. 1, the nose shield 48 fits over a patient's nose when administering medication with the nebulizer 10. The nose shield 48 keeps medication out of the patient's eyes and generally contained near the patient's nasal passages.

It would be understood that various changes in the details, materials, and arrangements of parts which have been described herein and illustrated in order to explain the nature of the invention may be made by those skilled in the art within the principal and scope of the invention, as expressed in the claims presented herein.

I claim:

1. A nebulizer comprising:
   two pair of concentric tubes for transporting fluid and pressurized gas to exposed ends of said concentric tubes;
   dual exit ports at said exposed ends for the simultaneous expulsion of parallel mist streams.

2. The nebulizer of claim 1 wherein said pairs of concentric tubes are in parallel and separated by the approximate average distance between the human nostrils.

3. The nebulizer of claim 1 wherein said nebulizer further comprises:
   a fluid reservoir into which said pairs of concentric tubes extend.

4. A nebulizer comprising:
   first and second parallel siphon tubes having similar dimensions, said siphon tubes simultaneously operable by pressurized gas creating a venturi effect;
   a reservoir for holding medication; and,
   wherein said siphon tubes are placed in contact with medication contained in said reservoir such that the medication is siphoned through and discharged from said tubes.

5. A nebulizer comprising:
   a base having a top, a bottom, and a central core;
   said central core of said base having an internal cavity;
   said bottom of said base having a hole through to said air cavity for receiving a pressurized gas;
   a cylinder with first and second open ends;
   said first end of said cylinder attaching to the top of said base, thereby forming a reservoir for holding liquids;
   two parallel gas transporting tubes, each having a first end and a second end, said second ends comprising tapered orifices;
   said first ends of said parallel gas transporting tubes oriented parallel to said cylinder and inserted through the top of said base such that pressurized gases flow from the cavity of said base through said gas transporting tubes;
   a removable cap fitted over the second end of said cylinder;
   two parallel liquid transporting tubes, each with first and second ends, said second ends tapering into small orifices;
   said liquid transporting tubes oriented perpendicular to and attached through said removable cap such that said second ends of said liquid transporting tubes jut above said cap; and,
   said parallel liquid transporting tubes oriented such that when the cap is fitted over the second end of said cylinder, the first ends of said liquid transporting tubes receive the second ends of said parallel gas transporting tubes, thereby enclosing the gas transporting tubes within the liquid transporting tubes.

6. The nebulizer of claim 5, further comprising:

a molded shield attached to said cap and oriented as to enclose a human nose when the nebulizer is in use.

7. The nebulizer of claim 5 wherein said liquid transporting tubes are integrally molded with said cap.

8. The nebulizer of claim 6 wherein said shield, said liquid transporting tubes, and said cap are integrally molded in a one-piece construction.

9. The nebulizer of claim 5 wherein said cylinder is constructed of a transparent material.

10. The nebulizer of claim 9 further comprising:

said cylinder having graduated volume markings corresponding to fluid levels within the cylinder.

11. The nebulizer of claim 5 wherein said gas transporting tubes are integrally molded with said base.

12. The nebulizer of claim 5 wherein said cylinder is integrally molded with said base.

13. A nebulizer comprising:

first and second parallel siphon tubes having similar dimensions;

first and second gas discharge tubes concentrically within said first and second parallel siphon tubes, respectively;

a reservoir for holding medication; and, wherein said siphon tubes are placed in contact with medication contained in said reservoir such that the medication is siphoned through and discharged from said tubes.

14. The nebulizer of claim 13 wherein the first and second gas discharge tubes pass through said reservoir for holding medication.

15. The nebulizer of claim 13 wherein said first and second parallel siphon tubes and first and second gas discharge tubes are relatively positioned such as to create a venturi effect when pressurized gas is introduced into said gas discharge tubes, thereby drawing medication from said reservoir into said siphon tubes.

16. The nebulizer of claim 15 wherein the medication is expelled from said siphon tubes in two mist streams having similar mist characteristics.

17. The nebulizer of claim 16 wherein said mist streams are suitable for the simultaneous administration of medication to both nasal passages on a human patient.

* * * * *